United States Patent [19]

DeVillez

[11] 4,451,480

[45] May 29, 1984

[54] METHOD OF TREATING ACNE USING OZONIZED MATERIALS

[75] Inventor: Richard L. DeVillez, New Braunfels, Tex.

[73] Assignee: James Howard Brown, Scottsdale, Ariz.

[21] Appl. No.: 369,163

[22] Filed: Apr. 16, 1982

[51] Int. Cl.$^3$ .......................................... A61K 31/335
[52] U.S. Cl. .................................... 424/278; 424/338
[58] Field of Search .................. 549/431; 424/278, 338

[56] References Cited

U.S. PATENT DOCUMENTS 925,590   6/1909   Neel ..................................... 549/431
2,356,062 8/1944  Johnson ............................ 424/76 X
4,163,800 8/1979  Wickett et al. ..................... 424/236

Primary Examiner—Leonard Schenkman
Attorney, Agent, or Firm—Wolder, Gross & Yavner

[57] ABSTRACT

A composition and method for the effective, nonirritating treatment of acne is disclosed. The method includes treatment of the affected area by topical application of an ozonized material derived by ozonizing various fixed oils and unsaturated esters, alcohols, ethers and fatty acids. The ozonized materials of the present invention have the ability to penetrate the comedone and deliver nascent oxygen directly to the acne microorganisms without the characteristic dryness and skin irritation associated with previous methods of acne treatment.

5 Claims, No Drawings

METHOD OF TREATING ACNE USING OZONIZED MATERIALS

BACKGROUND AND SUMMARY OF THE INVENTION

The present invention relates to topical compositions comprising ozonizing compounds derived from ozonolysis of fixed oils and unsaturated esters, alcohols, ethers and fatty acids. More particularly, the invention relates to compositions containing ozonized oil-soluble materials and the use of such compositions for the effective, nonirritating treatment of acne.

Acne is a condition of the human skin that affects many adolescents beginning about twelve years of age and continuing through the age of 25 years. During adolescence, the sebaceous glands enlarge, due to a hormonal stimulus, and increased sebum is produced and secreted on the skin. When the ducts through which the sebum flows are obstructed due to hyperkeratinization, a thickening and solidification of the sebum occurs, forming a solid plug known as a comedone. These lesions may eventuate to papules which in turn may evolve into pustules or deeper nodules which enlarge into cysts. The microorganism within the follicle of the skin is propionibacterium acnes, hereinafter referred to as P. acne. This microorganism produces an enzyme, lipase, which hydrolyzes triglycerides in the sebum to form free fatty acids which are responsible for the comedone formation. Acne is characterized by the presence of comedones, inflammatory papules, pustules or cysts, and the effects range from slight skin irritation to pitting and disfiguring scars.

Many compounds and compositions have been tested and prescribed for treatment of acne. A number of them have been fairly effective, but no complete cure for acne is presently available. The concept of the use of nascent or active oxygen to kill the anaerobic P. acne microorganism was introduced with the use of benzoyl peroxide. Such methods are described, for example, in the following U.S. patents: U.S. Pat. No. 3,535,422 to Cox et al; U.S. Pat. No. 4,056,611 to Young; U.S. Pat. No. 4,163,800 to Wickett et al; and U.S. Pat. No. 4,189,501 to Fulton.

However, the use of benzoyl peroxide is known to cause dryness and exfoliation, both of which are undesirable, particularly for teenagers and young adults.

By the present invention, there are provided therapeutic compositions for the treatment of acne, including the use of stable, ozonized oil-soluble compounds having the ability to penetrate the comedone and deliver nascent oxygen directly to the anaerobic P. acne microorganisms without the characteristic dryness and skin irritation which have been associated with the use of peroxide compounds.

The ozonolysis of oil-soluble compounds is well known in the art, being disclosed, for example, in the following U.S. patents: U.S. Pat. No. 925,590 to Neel; U.S. Pat. No. 984,722 to Twombly; U.S. Pat. No. 1,081,617 to Know; U.S. Pat. No. 2,083,572 to McKee; U.S. Pat. No. 2,897,231 to Niegowiski; U.S. Pat. No. 3,083,209 to Habib et al; and U.S. Pat. No. 3,145,217 to Horeczy et al.

The use of ozonized materials in formulations for medicinal purposes is disclosed in U.S. Pat. No. 1,210,949 to Knox and U.S. Pat. No. 2,356,062 to Johnson. Ozonized materials herein referred to as ozonides or ozonide compounds have been employed in the past for such uses as antiseptics, deodorizing agents and for treatment of dermatitis, inflammation of the nose and throat and for vaginal conditions. No method has been previously known, however, for the treatment of a skin disease, such as acne, by the use of ozonide compounds. Thus, the only method currently known for the treatment of acne utilizing the concept of the release of nascent oxygen for killing the anaerobic P. acne organisms is by the use of the peroxide compounds. However, due to the fact that such peroxide compounds are water-insoluble and cause skin irritation as previously discussed, it would be highly advantageous to employ an alternate method in which the nascent oxygen is released, without causing primary skin irritation such as is frequently experienced in the use of peroxide compounds.

The present invention provides just such an improved method for the treatment of acne, utilizing oil-soluble ozonides which have been found to demonstrate excellent characteristics in the killing of anaerobic P. acne, the organism active in the acne condition, by the release of nascent or active oxygen. The present invention is particularly beneficial, since the ozonide compositions have the capability to deliver nascent oxygen deep within the lesion where the infection exists, without causing primary skin irritation. The compositions of the present invention are applied topically to the afflicted area to release nascent oxygen. The ozonides are miscible with many organic cosmetic based materials, thus facilitating the incorporation of the ozonides into an elegant compound which is invisible on the skin during use. In one aspect of the invention, the ozonides are produced by the use of oxygen having a high degree of purity, thus eliminating the possibility of contamination of the ozone with nitrogen and other extraneous elements.

DESCRIPTION OF THE PREFERRED EMBODIMENTS

The compositions of the present invention must contain sufficient ozonide to be therapeutically effective while providing a cosmetically acceptable nonirritating treatment for acne. This composition provides oil-soluble ozonides in a formulation to provide a sustained release of nascent oxygen which is bacteriocidal to P. acne. A major requirement of the compositions is that the ozonide-containing preparations may be of many types, but must be nonirritating and cosmetically acceptable. This invention satisfies the above criteria by providing a topical, nonirritating acne treatment comprising a cosmetically acceptable base combined with at least one oil-soluble ozonide.

Any base material employed for the final product must be cosmetically acceptable and also must be nonirritating. The cosmetically acceptable base may, for example, be composed of a material such as: an ester such as isopropyl myristate, isopropyl palmitate, butyl stearate or propylene glycol dipelargenate; paraffin oils and waxes; animal and vegetable oils including coconut oil and derivatives, palm oil, corn oil and the like; lanolin derivatives; fatty alcohols such as isostearyl alcohol and straight chain alcohols containing from 6 to 18 carbon atoms; certain petroleum distillates which are toxicologically safe such as isoparaffin hydrocarbon solvents containing from 8 to 18 carbon atoms; and silicone fluids and waxes including the volatile silicones.

As the solvent component for the ozonide formulation, there may be employed the following; polyols such as propylene glycol; glycerine and alcohols such as anhydrous ethanol and isopropyl alcohol; other solvents such as acetone, and chlorinated solvents such as methylene chloride can be used in this invention if desired. A surface active agent such as an ethyoxylated fatty alcohol, a polyglycerol fatty ester or a sorbitan ester may also be used. Other commonly used formulation ingredients to improve cosmetic acceptability may be used, including fragrances and essential oils, preservatives, opacifiers, titanium dioxide, zinc oxide and similar materials. The formulation materials mentioned in this list are merely examples and are not intended to limit the invention in any way. In general, any non-aqueous material or mixtures thereof which are toxicologically safe for human use and are non-comedogenic in the concentrations used may be used as the carrier for the ozonide.

The ozonides employed in the present invention may be prepared by the Harries Ozonide Reaction with the basic reaction being described, for example, in U.S. Pat. No. 984,722 to Twombly; U.S. Pat. No. 2,083,572 to McKee and U.S. Pat. No. 2,356,062 to Johnson, all of which are incorporated herein by reference. The preparation of ozonides by the Harries Ozonide Reaction is well documented in the literature, being described, for example, in the Merck Index, 8th Edition, p. 1174, Section of Named Reactions. As stated in these references, the reaction can be carried out by treating the olefinic substrate with gaseous ozone. This is accomplished, for example, by sparging the olefin with ozone-laden oxygen. Basically, this reaction involves the treatment of an olefin with ozone to form an ozonide according to the following sequence:

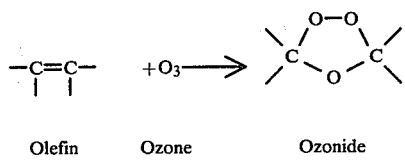

Olefin     Ozone     Ozonide

In general, any olefin can be so treated with gaseous ozone to form an ozonide. In order to be acceptable as an ingredient in the formulations described herein, the olefin should be nontoxic and cosmetically acceptable. The reaction products, upon hydrolysis of the ozonide on the skin, should likewise not produce toxic or skin-irritating substances. Examples of olefins that are acceptable for the production of ozonides to be employed in the present invention include fixed oils such as corn, olive, castor, sesame, jojoba and similar oils containing olefinic linkages. Other olefinic materials including fatty acids such as oleic acid, linoleic acid or elaidic acid and fatty alcohols such as oleyl alcohol can be ozonized to produce ozonides that are useful as active ingredients in the acne preparations herein described.

The ozonide used as the antibacterial preparation in this invention can be derived from fixed oils and unsaturated esters, alcohols, ethers and fatty acids olefins moeities of the general formula:

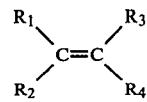

where for example $R_3$ and/or $R_4$ may be hydrogen (H) or:

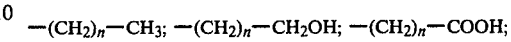

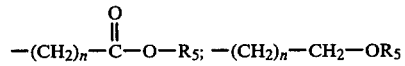

where
$R_5 = (CH_2)_n - CH_3$ and
n = an integer from 0 to 12.

NOTE: $R_1$ and $R_2$ can be any value given for $R_3$ and $R_4$ except that $R_1$ and $R_2$ cannot both equal H; also $R_3$ and $R_4$ cannot both equal H.

The compositions employed in the present invention may contain about 5 to 100% by weight of the ozonide. The active oxygen content in the compositions should be in the range from about 0.1% to about 15%, preferably from about 0.2 to about 2%, by weight of the ozonide component.

The amount of active oxygen that can be attached to a compound depends on the number of free double bonds available. The amount may generally range from 0% by weight to about 18% by weight of the compound. Thus, for example, as a sample of olive oil is ozonized, the olive oil will gain weight as the reaction proceeds. This increase in weight is due to the ozone absorbed by the olive oil. Olive oil, for example, can react with about 17 grams of ozone per 100 grams of oil. Of the 17 grams, approximately ⅓ or 5.7 grams is nascent or active oxygen. The maximum capacity of other olefins for absorbing ozone will in general depend on the amount of unsaturation contained in the molecule. For example, 2-butene theoretically will react with 82 grams of ozone per 100 grams of 2-butene and the active oxygen content would be about 27 weight % of the initial 82 grams.

It should be noted that a composition of the present invention for treating acne containing 1% by weight of active oxygen in the ozonide component could, for example, be prepared from ozonized 2-butene or olive oil that had been ozonized to a level greater than 1% by weight active oxygen. The procedure would involve simple dilution of these or any of the other above mentioned ozonides to the desired level with unozonized olefinic materials.

The compositions containing these ozonide preparations can be varied to produce a wide variety of finished products. Pomades, sticks, anhydrous creams, solutions, powders and gels are easily formulated by those experienced in the art. One olefin substrate that has been ozonized for medicinal use in olive oil. This fixed oil contains unsaturation that is readily transformed into ozonides by reacting it with ozone. Olive oil will react with ozone, forming ozonide at room temperature in a mildly exothermic reaction. As the olefinic groups are ozonized, the viscosity increases.

The acne treatment compositions of the invention may be further illustrated by the following nonlimiting examples:

EXAMPLE 1

A quantity of virgin Spanish olive oil was added to a gas washing bottle equipped with a fritted glass sparger. Medical grade oxygen was passed through a Union Carbide Ozonizer at 15 psig and a flow rate of 0.5 cu. ft./min. After a predetermined time, the olive oil samples showed a weight gain due to the reaction of ozone and the olefinic groups present in the oil being treated. The oxygen content of various samples was determined by the increase in weight to be from 1.94% to 8.27% by weight after ozonizing. Various ozonide samples were tested by chemical analysis and found to have active oxygen contents ranging from 0.35% to 1.58% by weight.

The ozonide products were subjected to microbiological testing using the organism P. acne under anaerobic atmospheric conditions. A ¼ inch antibiotic assay disc was placed on the inoculated Brain Heart Infusion (BHI) agar surface and 20 μl of product was delivered on the disc. After 48 hours incubation, the zone of bacteriocidal activity correlated well with the concentration of the test material. Nascent oxygen was released from the olive oil, diffused into the agar and was bactericidal to P. acne at all concentrations, greatest at the higher concentration of active ingredient. Further testing showed the olive oil ozonide to be noncomedogenic. This was an unexpected result due to the oily nature of the material. This ozonide without further modification was found to be non-irritating when applied to the skin. It is easily applied to acne lesions leaving an acceptable invisible film of ozonide. The active oxygen content of this formulation may be altered by either continuing the ozonizing to raise the active oxygen content or the oxygen content can be lowered by simple dilution with virgin Spanish olive oil or other suitable diluents.

Various other samples of olive, jojoba, sesame, castor and peanut oils were also ozonized as outlined above.

EXAMPLE 2

In this formulation, the solvency of acetone that is commonly used in acne preparations is incorporated into the ozonide-containing formula.

| Ingredient | Parts By Weight |
|---|---|
| Olive Oil Ozonide | 15.0 |
| Acetone | 15.0 |
| Dow Corning #344 Silicone Fluid (Polydimethylcyclosiloxane) | 68.8 |
| Menthol | 0.2 |

The resultant clear solution is cosmetically elegant and can be applied with the fingers or various types of applicators. Alternatively it could be conveniently packaged on towlette material in a foil package.

EXAMPLE 3

| Ingredient | Parts By Weight |
|---|---|
| Olive Oil Ozonide | 20.0 |
| Isopropyl Palmitate | 15.0 |
| Isopropyl Alcohol | 64.5 |
| Menthol | 0.5 |

This example demonstrates an alcohol-containing, elegant, invisible composition that can be applied as in Example 2.

The following formulations are liquids suitable for application with sponge-type or roll-on applicators.

EXAMPLE 4

| Weight % | Ingredient |
|---|---|
| 33% | $C_{12-15}$ Alcohols Benzoate (Finetex) |
| 13% | Ozonized Olive Oil |
| 54% | 344 Silicone Fluid (Dow Corning) |

EXAMPLE 5

| Weight % | Ingredient |
|---|---|
| 25% | Robane (Squalane) |
| 25% | Ozonized Sesame Oil |
| 50% | Acetone |

EXAMPLE 6

| Weight % | Ingredient |
|---|---|
| 35% | Neobee M-5 (vegetable triglycerides) |
| 20% | Ozonized Peanut Oil |
| 45% | 345 Silicone Fluid (Dow Corning) |

EXAMPLE 7

| Weight % | Ingredient |
|---|---|
| 10% | Ozonized Peanut Oil |
| 60% | Acetone |
| 30% | Robane (Squalane) |

The following formulation is a gel suitable for packaging in a jar or in the above applicators.

EXAMPLE 8

| Weight % | Ingredient |
|---|---|
| 10% | Synthetic Silica (Silicone Dioxide) |
| 50% | Mineral Oil, Light |
| 15% | 344 Silicone Fluid |
| 50% | Ozonized Olive Oil |
| 20% | $C_{12-15}$ Alcohols Benzoate |

The composition is applied topically to the skin of the patient by rubbing the ozonized product onto the areas being treated, one or more times daily. It should be therapeutically effective and cosmetically acceptable without skin irritation.

From the foregoing description of the present composition and method for the treatment of acne, it can be seen that the present invention provides an important contribution to the art to which the invention relates.

The invention may be embodied in other specific forms without departing from the spirit or essential characteristics thereof. The present embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed and desired to be secured by Letters Patent is:

1. A method for treating acne which comprises applying topically to an affected area an effective amount of an ozonide of fixed oils, esters, fatty acids, alcohols and ethers containing an olefin of the general formula;

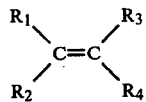

wherein: $R_3$ and/or $R_4$ may by hydrogen or:

$-(CH_2)_n-CH_3$; $-(CH_2)_n-CH_2OH$; $-(CH_2)_n-COOH$;

-continued

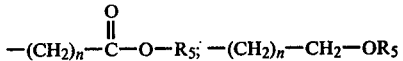

where $R_5=(CH_2)_n-CH_3$ and n=an integer from 0 to 12; with $R_1$ and $R_2$ being any value given for $R_3$ and $R_4$ with the proviso that $R_1$ and $R_2$ cannot both equal H and also $R_3$ and $R_4$ cannot both equal H.

2. The method of claim 1 wherein the active oxygen content of the ozonide material is from about 0.1% to about 15% by weight of the ozonide material in a cosmetically acceptable base.

3. The method of claim 2 wherein the active oxygen content of the ozonide material is from about 0.2% to about 2% by weight of the ozonide material.

4. The method of claim 1 wherein the ozonide is selected from the group consisting of the ozonides of olive oil, sesame oil, jojoba oil, castor oil and peanut oil.

5. The method according to claim 4 wherein the ozonide is selected from the group consisting of ozonized olive oil and jojoba oil.

* * * * *